United States Patent [19]

Allen

[11] 4,314,559
[45] Feb. 9, 1982

[54] NONSTICK CONDUCTIVE COATING

[75] Inventor: Richard E. Allen, Corning, N.Y.

[73] Assignee: Corning Glass Works, Corning, N.Y.

[21] Appl. No.: 102,886

[22] Filed: Dec. 12, 1979

[51] Int. Cl.³ ............................................. A61B 17/36
[52] U.S. Cl. .................. 128/303.14; 30/140
[58] Field of Search ........................ 128/303, DIG. 14; 30/140

[56] References Cited

U.S. PATENT DOCUMENTS

| Re. 29,088 | 12/1976 | Shaw | 128/303.17 |
|---|---|---|---|
| 3,071,856 | 1/1963 | Fischbein | 128/DIG. 14 |
| 4,161,950 | 7/1979 | Doss et al. | 128/303.14 |
| 4,232,676 | 11/1980 | Herczog | 128/303.14 |
| 4,248,231 | 2/1981 | Herczog et al. | 128/303.14 |

FOREIGN PATENT DOCUMENTS

| 1029363 | 5/1966 | United Kingdom . |
|---|---|---|
| 1178742 | 1/1970 | United Kingdom . |
| 1247734 | 9/1971 | United Kingdom . |
| 1476121 | 6/1976 | United Kingdom . |

Primary Examiner—Robert W. Michell
Assistant Examiner—T. J. Wallen
Attorney, Agent, or Firm—John P. DeLuca

[57] ABSTRACT

In a preferred embodiment, there is provided a conductive non-stick electrode for use with a hemostatic tissue cutting scalpel wherein, a first layer of conductive material having a textured working surface for contacting tissue is adherently deposited along the cutting edge of the scalpel, and a second coating of non-stick material is deposited thereon at least partially filling the textured surface, so that portions of the conductive material are exposed and the electrode is thereby conductive along said working surface but non-sticking while in contact with tissue.

14 Claims, 4 Drawing Figures

NONSTICK CONDUCTIVE COATING

BACKGROUND OF THE INVENTION

This invention relates to conductive coatings and specifically to a nonstick conductive coating for use with an electrosurgical cutting instrument.

Electrosurgical devices or surgical cutting blades, which are adapted to use radio frequency electrical energy in the performance of hemostatic surgery, are disclosed in commonly owned copending related United States patent applications of Herczog, U.S. Ser. No. 961,192, and Herczog et al., U.S. Ser. No. 961,189. Other such hemostatic surgical instruments are available in the prior art, for example, see U.S. Pat. No. Re. 29088 for a heated surgical scalpel. There are other variations on the concept of hemostatic surgery including systems utilizing electric discharge to cut and cauterize, and related systems such as shown in U.S. Pat. Nos. 4,161,950, 4,033,351 and 3,913,583.

While the concept involved in the present invention might be adapted for use in many of the aforementioned electrosurgical devices, it is best exemplified for its usefulness in the cutting instruments of the type disclosed in Herczog et al. (hereinafter the Herczog or RF blade). In a preferred system, electrical source generated hemostatic and cauterizing currents are carried to separate electrodes which are deposited near the edge of the blade. Moisture from incised tissue surfaces completes a circuit from one electrode to the other and the high frequency source generated currents pass through the tissue, generate heat and cause hemostasis in the vicinity of the electrodes.

In such a system it is possible for the blade to stick to the tissue in the incision, thereby causing apparent dullness of the blade. The problem is alleviated when non-stick coatings are used, however, because of the nature of non-stick materials, many tend to be fragile and are abraded easily. Thus, the non-stick properties tend to degrade in normal use, due in part to actual cutting, and partly due to the frequent wiping necessary in order to remove surgical debris adhered to the blade. When sticking is severe, the blade is unfit for further use and must be discarded. Further, when using the Herczog concept, the non-conductive nature of most non-stick films tends to interfere with the conductivity of the electrodes.

There are a number of patents in the prior art disclosing non-stick coatings. These patents mainly relate to the use of fluorocarbon polymers on razor blades for increasing their lubricity and enhancing the comfort of such shaving instruments while in use. Such arrangements are described in U.S. Pat. Nos. 4,012,551 and 3,754,329. There are also electrosurgical instruments having non-stick coatings, but none approach or contemplate the problems unique to RF blades.

Organic fluorocarbon materials such as those sold by E. I. DuPont de Neumoirs under the registered trademark TEFLON ® may be used in conventional instruments. However, since such materials are nonconducting it is difficult to achieve the conductivity required for RF applications. If the electrodes are insulated, they become ineffective for the purpose of hemostatic surgery in accordance with the Herczog blade concept.

The present invention solves many of the aforementioned problems by providing a conductive coating manufactured as the composite of a first layer of conductive material adherently deposited on the instrument and a second coating of non-stick material deposited on and within the first coating. The second coating at least partially fills microscopic irregularities or interstices in the first, such that the non-stick coating is able to adhere thereto. The nonstick coating is then partially removed while still moist such as by wiping, so that high profile points in the conductive coating are exposed, thus allowing the electrodes to be sufficiently conducting while exhibiting a satisfactory non-stick characteristic. The conductive layer is provided with sufficient roughness so that the non-stick coating will more firmly adhere thereto and resist erosion or peeling.

SUMMARY OF THE INVENTION

The invention may be described briefly as an electrically conductive non-stick coating for making electrical contact with electrically conductive external materials comprising, adherently interconnected masses of conductive and non-stick materials adherently deposited on a substrate. At least a portion of the conductive material is exposed for conduction, and the non-stick material interspersed therebetween inhibits sticking to the external materials.

In a preferred embodiment an electrically conductive non-stick coating for use in an electrosurgical cutting instrument is provided for carrying electrical source generated hemostatic and cauterizing currents to a portion of the instrument in contact with tissue. The electrically conductive non-stick coating comprises at least two coatings with a first coating of electrically conductive material adherently deposited on the instrument per se and having surface roughness and/or intersticies forming an exposed textured surface, and a second coating of a non-stick material adherently deposited over the first coating, so that the textured surface of said first coating is at least partially impregnated therewith. The second coating while still moist is partially removed to expose high profile points of the conductive textured surface. The remaining lower profile portions of the first coating adherently retain the non-stick material therein. The first and second coatings form a composite non-stick conductive coating with areas of exposed non-stick material and exposed conductive material. The non-stick areas render the cutting instrument resistant to sticking, and the exposed conductive high profile points enable the coating to conduct through its exposed portion.

DESCRIPTION OF THE PREFERRED EMBODIMENT

Figure 1:
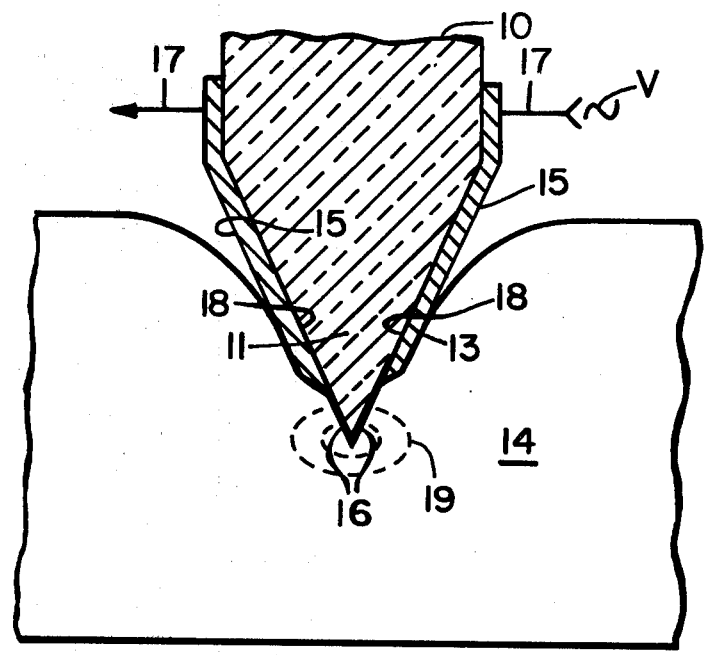
FIG. 1 is a schematic view of the Herczog blade concept referred to above.

Briefly, the illustration of FIG. 1 is a schematic of the Herczog type arrangement wherein a blade 10, preferably a glass or glass-ceramic material and having a cutting edge portion 11 is used to make an incision 13 in tissue 14. Conductive electrodes 15 are deposited on opposite sides of the cutting edge 11 and are separated by insulated space 16. Electrical connections 17 provide a means for impressing therein an alternating current electrical input voltage V from a source not shown. The interfaces 18 between the surface of each electrode 15 and the incision 13 are moist by virtue of the presence of physiological fluid (not illustrated). A circuit across electrodes 15 is completed via one or more paths 19 for current flow through the tissue 14. This described arrangement is discussed in greater detail in the copending U.S. patent application of Herczog et al. Ser. No. 961,189 referred to above. For purposes of explanation of the present invention, however, the description herein is sufficient.

Electrodes 15 may be deposited on the blade 10 by various means, but essential to the Herczog principle of operation is that they must be in electrical contact with a bridging medium (e.g. moist tissue and/or physiological fluid) in order to complete the circuit. If a non-stick coating is applied over the electrodes 15, the material must not insulate or short out the electrodes, but rather allow the circuit to be completed.

Figure 2:
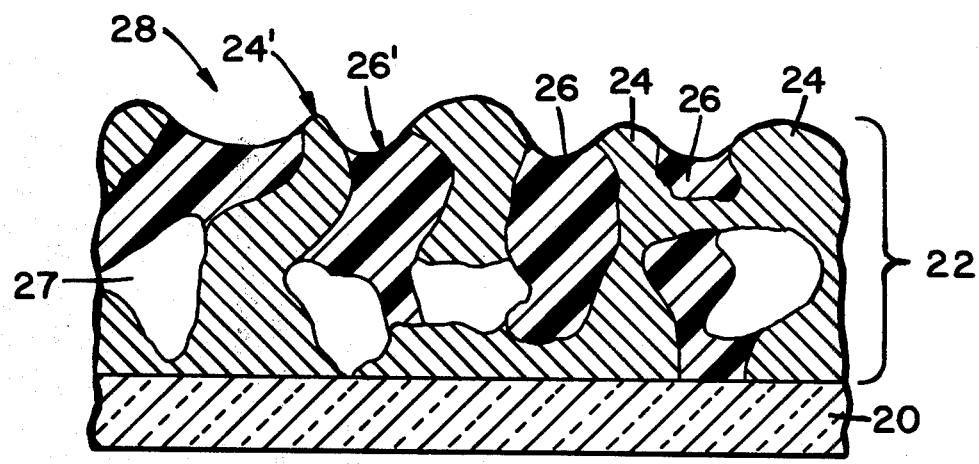
FIG. 2 is a side section of the conductive non-stick coating of the present invention.

In FIG. 2 one such possible arrangement for accomplishing this end is illustrated. A substrate 20, such as blade 10, supports a composite coating 22 which is comprised of conductive material 24 in an interconnected sintered textured mass, and non-stick material 26 at least partially filling rough spots or intersticies in the conductive material 24. Although the conductive material is continuous, open spaces 27 represent possible voids in the coating 22. An upper surface 28 of the coating 22 has exposed areas of conductive material 24 at conductive high profile points or areas 24'. Likewise portions of the non-stick material 26 lie near the upper surface 28 at non-stick profile points 26'.

An electrical connection (not shown) may be made with the conductive material 24. High profile points 24' would be in circuit therewith by the nature of the interconnected mass of the conductive material 24. Thus, the exposed high profile points 24' form interconnected conductive zones or islands (see FIGS. 3 and 4 and discussion hereinafter for details). A conductive material such as tissue coming in contact with the profile points 24' will form part of the electrical circuit. The surface 28 of the coating 22 exhibits non-stick characteristics as well, due to the presence of non-stick material 26 dispersed throughout the coating. (See FIG. 4 and discussion hereinafter for details.)

Before referring to the scanning electron micrographs of FIGS. 3 and 4, an embodiment of the present invention will be detailed by use of the following general example which is further detailed in Example 4 below.

EXAMPLE 1

Apply a precious metal paste, such as Englehart A3392 Ag, on a glass substrate to form electrodes. Fire to 550° C. for ten minutes. This provides a relatively rough porous surface. (See FIG. 3.)

Apply thereover a TEFLON ® primer, such as DuPont 850-300 mixed in the proper proportions with DuPont VM7799. While still wet, wipe the coated area with a Kimwipe ™. This serves to remove the insulating TEFLON ® from the high profile points 24' while leaving it adhered in the intersticies forming profile points 26'. In this manner, a TEFLON ® primer coating may be applied to most of the surface area 28, but conductance is still maintained. Bake the primer coating for 5 minutes at 270° C.

Apply a TEFLON ® overcoat, such as DuPont 852-201 and while wet, wipe as above.

Bake the overcoating for 10 minutes at 400° C. In this manner a non-stick, conductive electrode is obtained. The significance of this example is as follows.

Figure 4:
FIG. 4 is a scanning electron micrograph of a composite non-stick conductive coating of the present invention wherein the conductive material depicted in FIG. 3 is treated with a fluorocarbon material filling the intersticies thereof.

(1) A well adhered nonstick coating is obtained everywhere but on the high profile points 24' of the surface 28 (See FIG. 4.)

(2) The high profile points 24' on the electrode coating 22 allow the electrode to maintain its conductance.

(3) The major part of the electrode surface area is coated with a non-stick TEFLON ® created by profile points 26'. Moreover, other portions of the cutting instrument not shown may receive some non-stick coating.

Figure 3:
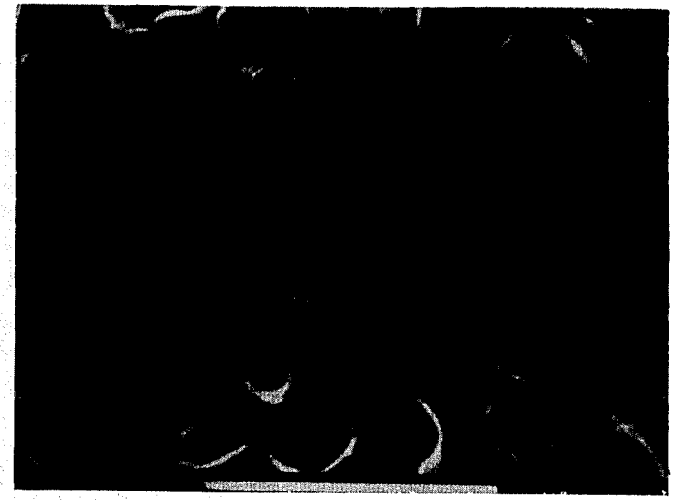
FIG. 3 is a scanning electron micrograph of the conductive electrode material deposited on a substrate illustrating surface texture.

Referring to FIG. 3, it can be seen that a paste of the type utilized in Example 1 above may be deposited on a glass or glass-ceramic or other substrate as desired. When the paste is fired to a moderately high temperature such as 550° C. for the period indicated, it sinters and forms the interconnected mass of material. The light gray areas represent the sintered mass and the darker areas represent openings or intersticies therebetween which are tunnel-like formations (nooks, crannies, etc.) from one light area to another. The sintered mass in the micrograph has a relatively rough surface so that certain portions thereof are at higher microelevations than others. After the TEFLON ® material deposited on the sintered mass of FIG. 3 is wiped and fired, a composite coating results as illustrated in FIG. 4. Certain portions of the sintered mass (i.e. lightest areas) remain elevated above other portions of the mass. The textured somewhat darker areas in FIG. 4 show the location of the non-stick material which has now filled the intersticies in the sintered mass, so that, the non-stick material has a strong foothold in the textured surface of the conductive material. By wiping the surface of the sintered mass after applying the non-stick material, the high profile points 24' (lightest areas) are exposed, yet most of the surface of the sintered mass is covered with a non-stick material. Thus the surface is both conducting through the high profile points 24' and non-sticking over the remaining areas 26' filled with the non-stick material.

The surface texture of the materials illustrated in FIGS. 3 and 4 may be estimated from the scale of the micrographs. In both FIGS. 3 and 4 the scale shown is five microns/inch. Thus the particle sizes of the sintered silver may be estimated at about 1–5 microns. The spaces or intersticies appear to be about the same sizing and relatively evenly dispersed throughout the sintered mass. In FIG. 4 the TEFLON ® appears to be a sintered mass interspersed within the intersticies of the conductive coating. It appears that about half of the high profile points 24' remain exposed after processing. The non-stick characteristics of the coating may result from the lack of large surfaces to which work material (e.g. tissue) can stick. That is, the TEFLON ® and conductive materials are broken up on the surface 28 of the coating 22 into islands of respective non-stick and conductive zones.

Example 1 above sets forth a procedure for making a composite conductive non-stick coating using a conductive silver paste and a TEFLON ® over coat including a primer coat. The examples below set forth other conductive non-stick coatings with comments on observed results. In some of the following examples reference will be directed to FIG. 1 for blade component terms.

EXAMPLE 2

Non-Stick Conductive Coatings Applied Over Sputtered Platinum Electrodes

Electrodes similar to 15 in FIG. 1, are applied by a photo-resist and sputtering process. They extend to within 0.005" to 0.010" of the cutting edge 11.

All work in this section was done with TEFLON® primer only. TEFLON® primer enhances non-stick and adherence of the TEFLON® overcoat. The latter composition is optimized for its non-stick properties.

The DuPont TEFLON® materials used throughout the following examples are:

Primer, 850-300 VM7799 mixed 100:36 respectively by weight. This primer was then diluted with distilled H$_2$O 50:50 by weight.

Overcoat, 252-201.

(a) Primer and Ag Powder Mixes

Mix TEFLON® primer and Ag powder in such a ratio that the mix is conducting.

Materials

DuPont TEFLON® primer noted above.
Acheson Colloids Co.—silver pigment RW21790 (a powder)
Engelhard Industries—silver powder A-2206.

Method

The primer and Ag powders, each in turn, were well mixed on 75×50 mm microslides, using a spatula. Proportions were narrowly varied about the ratio where the mixtures became conductive. The mixtures were brushed out into thin uniform coatings, using a camel's hair brush, and, after a 90° C.-10 minute drying bake, were fired at the recommended temperature of 400° C. for 10 minutes.

Results

The non-conductive coatings brushed easily into good-looking thin films. The conductive mixes, however, coagulated on mixing and were not brushable. Furthermore, as the amount of Ag powder was increased, the adherence of the coatings decreased and failed to pass a thumbnail scrape test.

(b) Primer-Ag Paste Mix

Mix TEFLON® primer, which is an aqueous suspension, with a compatible aqueous suspension of Ag paste. Such an Ag paste contains water based binders for improved adherence, and wetting agents for improved miscibility.

Materials

DuPont TEFLON® primer, noted above.
DuPont No. 4535 Ag paste.

Method

These two materials were thoroughly mixed 50:50 by volume on a 75×50 mm microslide, using a spatula. The mixture was then brushed out on a microslide and on the edge of a scalpel, covering the entire Pt electrode area previously formed thereon, including the edge. The cutting edge 11 was then doctored with a piece of moistened blotting paper. In essence, this amounts to drawing the blade cutting edge 11 lightly across the edge of the blotter in the cutting mode. In this case, the uniformity of coating removal from the cutting edge was barely acceptable for coating evaluation. After drying at 90° C. for 5 minutes, these coatings were baked-on at 400° C. for 10 minutes.

Results

The coating was conductive.
The coating did not quite resist removal by the thumbnail scrape test.

In a moderate amount of rabbit surgery, this coating exhibited excellent non-stick properties. However, later microscopic inspection revealed that the coating had flaked-off and worn-off about 0.015" to 0.020" back from the cutting edge.

(c) Kim-wiped Primer on Acheson 504SS

The concept here was to impregnate the surface of 504SS with primer. The former is fairly rough compared to sputtered Pt.

Materials

DuPont primer as noted above.
Acheson Colloids Co.—Electrodag 504SS. This is an Ag powder in an organic vehicle containing an organic binder.

Method

The 504SS was brushed onto 75×50 mm microslides and baked for 20 minutes at 150° C. Primer was then brushed onto ½ of the coating, and immediately, while still wet, wiped off with a Kim-wipe. The microslide was then baked at 400° C. for 10 minutes.

Results

The area with Kim-wiped primer was a light straw color, indicating that some primer had impregnated the surface of the 504SS.

The coated-wiped area was conductive.

The primed 504SS could not be removed with SCOTCH® brand tape; the unprimed 504SS was easily removed. Thus, it appeared that the primed 504SS had much improved non-stick properties.

The 400° C. firing, necessary for sintering the primer, degraded the 504SS adherence.

(d) Kim-wiped Primer on Pt Electrodes

The concept here was to impregnate sputtered Pt electrodes with primer.

Materials

DuPont TEFLON® primer as noted above.

Method

Primer was brushed onto the electrode and an adjoining bare glass area, including the uncoated strip next to the cutting edge, and immediately, while still wet, wiped off with a Kim-wipe. The coating was then baked at 400° C. for 10 minutes.

Results

The coated-wiped electrode was conductive.
The coated-wiped area, especially the electrode area, appeared to have a very thin coating. It visually appeared as if oil had been applied and then wiped off.

With SCOTCH ® brand tape, the coated areas had much better non-stick properties than the uncoated areas.

It appeared that wiping-off the primer from the electrodes while wet removed it from the high profile points, thus allowing the electrode to be conducting, whereas the primer remained on the rest of the electrode surface, thus allowing it to be non-stick.

General Observations

During the work described above, the following observations were also made about the nature of TEFLON ® primer and the substrates to which it was applied:

The film can be scraped-off a microslide with a razor, but it leaves behind a non-stick "memory" in the scraped-off area, as qualitatively determined by scraping the razor over the scraped-off area and a "virgin" area of glass. The film can be partially scraped-off the high profile points only. The checks, valleys, crevices, depressions, etc. in the surface appear to be permeated. The scraped-off areas are much more non-stick than "virgin" areas when tested with SCOTCH ® brand tape.

EXAMPLE 3

3. The Ag Paste Electrode

The purpose here was to utilize what had been learned in Example 2 above. It was desired to develop electrodes with a rougher surface finish than the sputtered Pt in order to increase the amount of retained TEFLON ® primer after the Kim-wiping operation. It was thought that fritted precious metal pastes, which are porous, would allow the TEFLON ® to permeate and "lock into" their porous structure, thus promoting good TEFLON ® adherence. It was thought that the chief problem here would be in obtaining the necessary uniformity of the non-metallized strip, extending from 0.005" to 0.010" near the cutting edge.

Material

Engelhard Industries Backlite Silver Paste A-3392.
Drakenfeld 324 Oil of Turpentine.

Method

Dilute the Ag paste with the 324 oil 5:1, respectively. Coat the electrode area with this paste, including the edge, with a camel's hair brush.

Immediately, while the paste was still viscous, the blade cutting edge 11 was drawn lightly across the edge of a piece of dry blotting paper with the blade in the cutting mode as per Example 2 above.

Dry bake 10 minutes at 150° C.

Fire four (4) such coated scalpels at 500° C., 550° C., 600° C., and 650° C., respectively.

Results

Uniformity of the wiped-off or uncoated strip 16 next to the cutting edge 11 was much better than that obtained before in Example 2, possibly due to the oil vehicle used in the Ag paste. On these four blades uniformity of the coating near the cutting edge 11 varied by about 0.005", ranging on one blade from about 0.003" to 0.008" from the cutting edge 11 and on another from about 0.005" to 0.010".

On a razor blade scrape test for adherence, the 500° C. fired scalpel, on which the Ag paste was only partially sintered, still had better adherence than the Acheson 504SS (Example 2C above). Ag paste adherence on the 500° C., 600° C., and 650° C. blades improved with firing temperature. All of the latter three were excellent.

The 650° C. blade above was tested for electrode erosion by immersion in a 0.85% by weight NaCl solution. With the blade partially immersed, a 50 V R.F. continuous wave (square) was applied. This produced vigorous boiling, but no visible electrode disintegration. Subsequent microscopic inspection revealed that this very harsh treatment had indeed eroded the electrodes by about 0.002".

EXAMPLE 4

The purpose here was to utilize what had been learned about TEFLON ® and silver paste in Examples 2 and 3 above.

(a) Kim-wiped Primer and Overcoat Materials

DuPont TEFLON ® primer and overcoat noted in Example 1.

Engelhard Ag paste A-3392.

Method

Ag paste electrodes were applied to twelve Corning Code 99VMT scalpels by the procedure described in Examples 2b and 3 above.

TEFLON ® primer was applied, wiped while wet and baked 5 minutes at 275° C.

TEFLON ® overcoat was then applied over the primer in the same manner and baked 10 minutes at 400° C.

| Scalpel No. | Ag Firing Temp. (10 Min.) | Results Use |
|---|---|---|
|  | 650° C. | Heavy: At least 34 4" incisions (rabbit surgery) plus follow-up testing (unquantified). |
| 2 | 650° C. | Heavy: At least 16 4" incisions (rabbit surgery) plus follow-up testing. (Unquantified) |
| 3 | 550° C. | Moderate: All of these |
| 4 | '' | scalpels (3-12) were evaluated |
| 5 | '' | using both rabbit and |
| 6 | '' | dog surgery. None had as |
| 7 | '' | harsh usage as blades #1 |
| 8 | '' | and #2 above. |
| 9 | '' |  |
| 10 | '' |  |
| 11 | '' |  |
| 12 | '' |  |

All the scalpels gave essentially the same qualitative results. They could be cleaned of most tissue debris with a dry piece of surgical gauze immediately after making a hemostatic cut. The scalpels did not stick to tissue or "drag" during the actual cutting operation. Some good hemostasis was observed even when a considerable amount of tissue debris was allowed to build up on the electrodes. Post-surgery microscopic inspection revealed some tissue adherence on a ½" long section of the bare glass 0.005" wide strip (16 in FIG. 1) next to the cutting edge 11 on scalpel #1 only. This particular scalpel was given a great deal of use, possibly much more than one would expect in actual service.

(b) Kim-wiped Primer Only

Apply Ag paste in Example 4a and primer only. Kim-wipe as above. Materials and method were the same as in Example 4a above except that the primer was baked 10 minutes at 400° C.

| Scalpel No. | Ag Firing Temp. (10 Min.) | Use |
|---|---|---|
| 13 | 550° C. | Moderate: Similar to #'s 3-12 in Example 4a. |
| 14 | 600° C. | Moderate: Similar to #'s 3-12 in Example 4a. |

13 performed substantially identically to the scalpels discussed in Example 4a, which had both primer and overcoat. #14 initially showed somewhat poorer non-stick properties, but then performed the same as #13.

(c) Diluted Primer

Apply Ag paste as in 4(a), therefore apply TEFLON ® overcoat diluted with four parts distilled water to one part overcoat. Kim-wipe, air dry and fire ten minutes at 400° C.

The blade hemostasis performed as well as an uncoated device and exhibited good nonstick characteristics. The dilution of the TEFLON ® overcoat appears to qualitatively increase the hemostatic conductivity of the electrodes but resulting changes in physical characteristics of the blade could not be measured quantitatively. The hemostasis improved and the non-stick remained excellent.

Conclusions from Examples 1-4

(a) Adherent mixtures of TEFLON ® primer and Ag powder were not satisfactory. Adding enough Ag powder to the primer to make it conductive caused coagulation and loss of adherence. However, nonabrasive use of the coating might be practical.

(b) TEFLON ® primer and a commercial water based Ag paste mix showed some promise when applied over the sputtered Pt electrodes. Although workable its durability was not quite satisfactory for prolonged cutting. Because of this, the complexity of the overall sputtering process, and later more promising developments in the Ag paste systems of Example 4, this approach although workable was considered unattractive.

(c) It was found possible to impregnate the surface of Acheson 504SS Ag conducting paste with TEFLON ® primer without losing conductance. Unfortunately, the subsequent 400° C. bake, necessary for fusing the primer, degraded the 504SS adherence, which was initially borderline.

(d) By Kim-wiping while the primer coating was still wet, it was found possible to apply a very thin non-stick coating to the sputtered Pt electrode without loss of conductance. This approach is marginally preferred but the results of Example 4 are thought to be more promising and thus preferred.

(e) It was observed that only a very thin film of TEFLON ® primer is necessary to impart non-stick properties. Further the primer cannot be entirely scraped from a rough surface because once applied, it tenaciously adheres to the nooks, crannies, valleys, depressions, etc.

(f) The Ag paste electrode, which may be brush or screen printed, presents a rougher surface and a porous body for subsequent TEFLON ® primer impregnation. The electrode is simple to apply by this method and eliminates complex photo-resist and sputtering operations.

(g) By Kim-wiping while the primer and/or overcoat is still wet, it is found possible to impregnate the Ag paste electrode without loss of conductance.

(h) Diluted TEFLON ® applied as an overcoat appears to be a preferred embodiment since hemostasis is least affected by the non-stick coating.

Other materials may be useful in the preparation of conductive non-stick coatings such as fluorosilicates, and silicones.

Examples of materials useful for the conductive coating 24 include the materials mentioned above as well as gold, rhodium, palladium and other noble or semi-noble metals. Still other oxidizable materials such as molybdenum could be useful if fired in an inert atmosphere.

The ratio of exposed conductive areas 24' to nonconductive areas 26' may range respectively from about 20/80 to about 80/20, however the preferred range is about 40/60 to about 60/40. The optimum for a Herczog blade may be closer to 40/60, so that conductivity of a composite coating 22, such as in FIG. 4, is about 90% that of the uncoated surface of FIG. 3.

While not completely understood, it appears that the non-stick mechanism is that the TEFLON ® blocks the adhesion of the tissue to the crevices in the conductive electrodes. With intersticies filled, tissue has little or no surface area to adhere to.

In order to provide a cutting edge similar to that described in the Herczog et al. disclosure the methods described in Examples 2b, 3 and 4 above are preferred. The specific formulation of Example 4c appears to exhibit the best results to date.

What is claimed is:

1. In an electrosurgical cutting blade having deposited thereon electrodes for contacting tissue and carrying electrical source generated hemostatic and cauterizing currents thereto, each electrode comprising an electrically conductive non-stick composite coating deposited near the cutting edge thereof including: a first coating of electrically conductive material adherently deposited on said blade near the cutting edge, said first coating having an exposed textured surface; a second coating of nonstick material adherently deposited on said blade at least over said first coating to the extent that the textured surface of said first coating, in the form of a sufficiently roughened mass having interconnected intersticies forming locations for the secure adhesion of the non-stick material therein, is at least partially filled therewith, portions of said first coating in the form of interconnected islands being exposed and conductive, and the second coating imparting non-stick characteristics to the blade.

2. The electrode of claim 1 wherein the surface texture of the first coating is in the order of about 1-5 microns.

3. The electrode of claim 1 wherein the first coating is comprised of a corrosive resistance metal.

4. The electrode of claim 1 wherein the first coating is comprised of metals selected from the group consisting essentially of silver, platinum, rhodium, palladium, gold, molybdenum.

5. The electrode of claim 1 wherein the second coating is comprised of organic material selected from the group consisting essentially of fluorocarbons, silicones, and fluorosilicates.

6. The electrode of claim 1 wherein the first coating is a conductive material in a colloidal suspension fired from about 500° to about 650° C.

7. The electrode of claim 1 wherein the conductive material is fired at 550° for 10 minutes.

8. The electrode of claim 7 wherein the second coating is applied in liquid form and partially removed by wipe application and fired to an adherence temperature.

9. The electrode of claim 8 wherein the second coating is fired at about 400° C. for 5-10 minutes.

10. The electrode of claim 1 wherein the second coating is smoothed by wipe application to remove excess coating and to expose portions of said first coating.

11. The electrode of claim 1 wherein the second coating includes at least one prime coat of fluorocarbon primer material being smoothed so as to expose portions of the first coating.

12. The electrode of claim 1 wherein said second coating is a water soluble fluorocarbon diluted with about four parts water.

13. The electrode of claim 1 wherein the first coating is first applied to the cutting instrument along the cutting edge and is removed by engagement with a doctoring surface.

14. The electrode of claim 1 wherein the first coating is applied to the cutting instrument by screen printing.

* * * * *

UNITED STATES PATENT AND TRADEMARK OFFICE
CERTIFICATE OF CORRECTION

PATENT NO. : 4,314,559
DATED : February 9, 1982
INVENTOR(S) : Richard E. Allen

It is certified that error appears in the above—identified patent and that said Letters Patent are hereby corrected as shown below:

Column 2, line 68, after "bly" cancel "a" and insert --of--.

Column 8, line 39, under the column marked "Scalpel No." insert --1--.

Column 10, line 62, "resistance" should be --resistant--.

Signed and Sealed this

Twenty-eighth Day of December 1982

[SEAL]

Attest:

GERALD J. MOSSINGHOFF

Attesting Officer     Commissioner of Patents and Trademarks